United States Patent [19]

Brown et al.

[11] 4,108,904

[45] Aug. 22, 1978

[54] PROCESS FOR THE PREPARATION OF M-PHENOXYBENZALDEHYDE

[75] Inventors: Dale Gordon Brown, Hopewell, N.J.; William Wayne Brand, Painesville, Ohio

[73] Assignee: American Cyanamid Company, Stamford, Conn.

[21] Appl. No.: 726,017

[22] Filed: Sep. 22, 1976

[51] Int. Cl.² .............................................. C07C 45/00
[52] U.S. Cl. ........................ 260/600 R; 260/612 R; 204/158 HA
[58] Field of Search ........... 260/612 R, 600 R, 651 R, 260/599; 204/158 HA

[56] References Cited

U.S. PATENT DOCUMENTS

| 2,816,144 | 12/1957 | Harris | 260/599 |
|---|---|---|---|
| 2,817,632 | 12/1957 | Mayor | 260/651 R X |
| 2,817,633 | 12/1957 | Mayor | 260/651 R UX |
| 3,442,960 | 5/1969 | De Puy et al. | 260/651 R |
| 3,448,156 | 6/1969 | Taussig et al. | 260/599 |
| 3,624,157 | 11/1971 | Ingwalson | 260/599 |

FOREIGN PATENT DOCUMENTS 809,867   1/1974   Belgium .............................. 260/613 R

OTHER PUBLICATIONS

B. Y. Libman et al.; Zhurnal Prikladnoi Khimii, vol. 39, No. 7 (1966), pp. 1669–1670.

*Primary Examiner*—Bernard Helfin
*Attorney, Agent, or Firm*—H. G. Jackson

[57] ABSTRACT

This is a novel process for the preparation of m-phenoxybenzaldehyde, a useful and valuable intermediate for the synthesis of pyrethroid type pesticides. The process comprises halogenation of m-phenoxytoluene on the side chain, in an inert solvent and in the presence of free radical initiators or strong light to a mixture of the corresponding mono and dihalo derivatives, and conversion of the mixture to m-phenoxybenzaldehyde by a Sommelet-type reaction.

10 Claims, No Drawings

PROCESS FOR THE PREPARATION OF M-PHENOXYBENZALDEHYDE

It is known, that alkyl and aralkyl mono halides can be converted to their corresponding aldehydes via an intermediate quaternary salt, prepared from said alkyl and aralkyl halides and hexamethylenetetramine. Hydrolysis of the quaternary salt affords the desired aldehyde. [M. Sommelet, *Compt. Rend.* 157, 852(1913) and *Bull. Soc. Chim. France* [4] 23, 95 (1918)].

In a recent article, B. Ya. Libman et al. disclose the preparation of benzaldehyde via a Sommetlet reaction from mixtures of benzyl and benzal chloride [*Zhurnal Prikladnoi Khimii*, 39 (7), 1669-70(1966)]. This article, however, is limited to the preparation of benzaldehyde per se.

Belgian Pat. No. 809,867 (1974) granted to Sumitomo teaches the direct chlorination of m-phenoxytoluene in the presence of phosphorus trichloride at temperatures above 220° C to obtain a mixture of mono and dihalo derivatives. The examples included in the patent clearly show, that at temperatures below 220° C extensive ring halogenation takes place, and the products thus obtained are contaminated to a degree unacceptable with the unwanted side products e.g. 3-phenoxy-6-chlorotoluene. This patent does not anticipate, nor is it predictable therefrom, that m-phenoxytoluene can be halogenated in inert solvents at relatively low temperatures in the presence of certain free radical initiators or strong light to obtain a mixture of the mono and dihalo derivatives with minimal contamination by ring halogenated by-products.

A useful and valuable intermediate for the synthesis of a number of economically important, highly effective pyrethroid type pesticides is m-phenoxybenzaldehyde of formula (I):

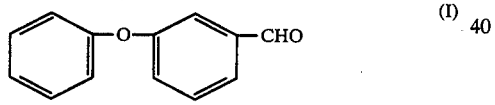

Conventionally, the aldehyde of formula (I) can be prepared by dihalogenating m-phenoxytoluene (IV) and hydrolyzing the thus obtained dihalo derivative (III) to obtain the desired aldehyde (I) as hereinbelow graphically illustrated:

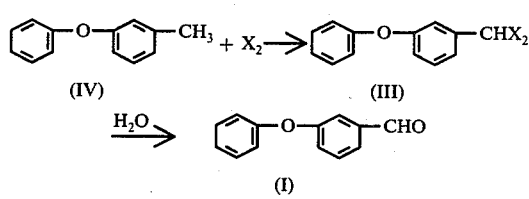

wherein X is a halogen.

Unfortunately, the above described route is not entirely satisfactory, since in the course of the halogenation reaction significant amounts of mono and trihalomethyl analogs of the desired formula (III) compound are also formed. Additionally ring halogenation also occurs. Thus, conventional halogenation affords a mixture of products, and since not all of them can be directly hydrolyzed to the desired aldehyde of formula (I), the latter is obtained in poor yields.

Indicative of the difficulties encountered in the halogenation of m-phenoxytoluene is the hereinabove cited Belgian Patent, which teaches that temperatures in excess of 220° C are necessary during the halogenation of m-phenoxytoluene in order to avoid and/or minimize the formation of the above referred-to undesirable by-products.

Surprisingly, we now find that by the novel halogenation process of the invention, m-phenoxytoluene can be halogenated under relatively mild conditions in an effective solvent to the reactants in the temperature range of preferably about the boiling point of the solvent selected. Advantageously, an effective free radical initiator, for example, lauroyl peroxide, 2,2'-azobis-(2-methylpropionitrile), 2,t-butylazo-2-cyanopropane, benzoylperoxide and the like is added to the reaction mixture in amounts of 0.1% to 10% by weight and preferably 1.0% to 10% by weight of m-phenoxytoluene, or in lieu of the initiator, the reaction mixture may be irradiated with a strong light source, such as a sunlamp, when the halogenating agent is bromine or chlorine.

Next, a halogenating agent, for example, bromine, chlorine or sulfuryl chloride is added to the above reaction mixture in amounts of 1.2 to 2 molar equivalents per mole of m-phenoxytoluene over a period of time from 1 to 24 hours, or until the reaction is essentially complete. The product thus obtained is a mixture of the mono (II) and dihalo (III) derivatives of m-phenoxytoluene, wherein the mixture is virtually free of, or contains only a small amount of, the above referred-to undesired impurities. The above reaction may be graphically illustrated as follows:

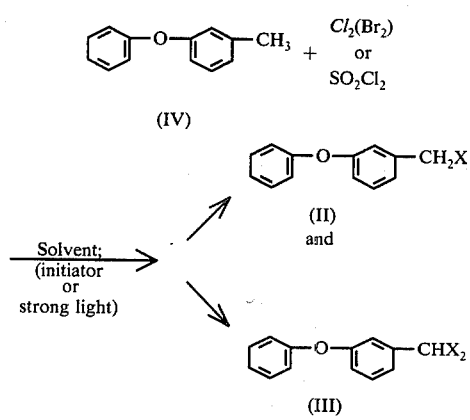

wherein X is bromine or chlorine.

Advantageously, we have found that the above mixture of the compounds of formulae (II) and (III) can be converted to the desired m-phenoxybenzaldehyde (I) by a Sommelet type of reaction. Thus, the above halogenation mixture consisting of compounds of formulae (II) and (III) is reacted with a 1 to 2 molar equivalent of hexamethylenetetramine in a solvent of aqueous $C_1-C_3$ alcohols or $C_2-C_3$ alkanoic acids. Next, the mixture is hydrolyzed in an aqueous mineral acid (e.g. hydrochloric acid) at the reflux in about 1 to 4 hours to afford the desired m-phenoxybenzaldehyde in satisfactory yields. The aldehyde (I) is recovered from the reaction mixture by standard laboratory procedures, e.g. extraction, steam distillation and the like and purified, if desired. The above reaction may be schematically illustrated as follows:

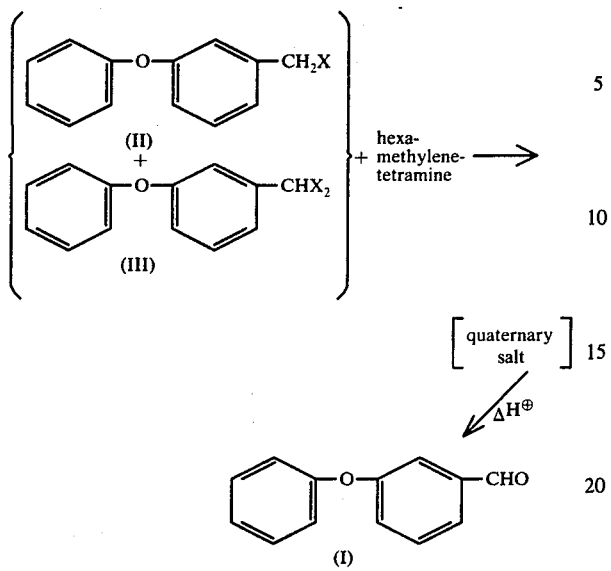

As stated above, the novel halogenation process of the present invention yields the mono and dihalo derivatives of formulae (II) and (III) under relatively mild conditions and free of significant amounts of contaminants, such as ring halogenated derivatives of m-phenoxytoluene. Consequently the halogenation mixture may be used without further purification in the preparation of the valuable m-phenoxybenzaldehyde intermediate.

The following non-limiting examples further illustrate the process of the invention.

EXAMPLE 1

Preparation of m-phenoxybenzaldehyde

A. To a refluxing mixture of m-phenoxytoluene (36.8 g; 0.199 mole) in carbon tetrachloride (150 ml), irradiated with a 275 W. G.E. Sunlamp, bromine (64.0 g; 0.400 mole) is added dropwise at a rate such that there is no color build-up in the reaction mixture. After 4 hours at reflux, the mixture is concentrated in vacuo to afford 75.0 g of a light brown oil. The proton nuclear magnetic resonance spectrum (NMR) shows a ratio of about 9:1 for the dibromo derivative ($\delta$ 6.55 for the benzylic proton) vs. the monobromo derivative ($\delta$ 4.4 for the benzylic proton), in $CDCl_3$.

B. A mixture of the mono and dibromo derivatives (22.5 g), hexamethylenetetramine (19.0 g), glacial acetic acid (27 ml) and water (27 ml) is heated at reflux for 2 hours. Concentrated hydrochloric acid (31 ml) is then added and the mixture refluxed for 45 minutes. The mixture is cooled, extracted with ether, the ether extract is washed with dilute acid and dilute alkali and dried over anhydrous magnesium sulfate. The ether is then removed in vacuo to afford 12.0 g of m-phenoxybenzaldehyde as a light brown oil. The structure is confirmed by NMR which shows the aldehydic proton at $\delta$ 9.95 and the aromatic protons at $\delta$ 7.25 (multiplet) in the ratio of 1:9 (in $CDCl_3$). The infrared (IR) spectrum shows the carbonyl group at 1680 $cm^{-1}$, neat.

EXAMPLE 2

Preparation of m-phenoxybenzaldehyde

A. A mixture of m-phenoxytoluene (20.0 g; 0.109 mole), 2,2'-azobis-(2-methylpropionitrile) (AIBN; 1.89 g) and carbon tetrachloride (80 ml) is heated at reflux and a solution of sulfuryl chloride (22.0 g; 0.163 mole) in carbon tetrachloride (80 ml) is added dropwise over 1.5 hours. The reaction mixture is heated at reflux overnight and is then concentrated in vacuo to afford 25.8 g of an oil. This oil is estimated to contain 66% of the monochloro and 29% of the dichloro derivative by NMR.

B. A mixture of the above oil (14.2 g), hexamethylenetetramine (17.1 g) and 60% aqueous ethanol (85 ml) is heated at reflux for 4 hours. The mixture is cooled, acidified with dilute hydrochloric acid, and is extracted with ether. The ether extract is dried over magnesium sulfate, concentrated in vacuo and the 10.1 g residual oil is distilled at 120° C to 130° C/0.05 mm to afford 7.5 g of m-phenoxybenzaldehyde.

The mass spectrum of the aldehyde shows no chlorine present in the product, indicating that no ring-chlorination occurred during the chlorination step.

EXAMPLE 3 to 14

Evaluation of sulfuryl chloride as a chlorinating agent for the side chain chlorination of m-phenoxytoluene under various reaction conditions In the following experiments, m-phenoxytoluene, freed of any residual phenolic impurities by prior washing with alkali and/or filtering through silica gel, is used.

General Procedure

A solution of sulfuryl chloride (5.46 g; 0.0405 mole) in carbon tetrachloride (20 ml) is added dropwise to a refluxing solution of m-phenoxytoluene (IV; 5.0 g; 0.024 mole), 2,2'-azobis-(2-methylpropionitrile) (AIBN; 0.05 g) in carbon tetrachloride (20 ml). After the addition is completed, the solution is heated at reflux for 18 hours. The solvent is then evaporated in vacuo and the residue analysed by vapor phase chromatography (VPC) and by proton nuclear magnetic resonance spectrum (NMR).

By the above procedure, using different solvents and/or catalysts a set of data is obtained, the summary of which is given in Table I, appended hereto.

Table I

| Example | Initiator | Initator as % by wt. of (IV) | Solvent | Reaction Temp ° C | Results by VPC | Results by NMR |
|---------|-----------|------------------------------|---------|-------------------|----------------|----------------|
| 3 | AIBN | 10 | Neat | 75–80 | Mostly Ring Chlorination | Mostly Ring Chlorination IV - 6% |
| 4 | AIBN | 1 | $CCl_4$ | Reflux | $CH_3$ Chlorination | Monochloro-59% Dichloro-35% IV - 4% |
| 5 | AIBN | 10 | $CCl_4$ | Reflux | $CH_3$ Chlorination | Monochloro-61% Dichloro-55% IV - 4% |
| 6 | AIBN | 10 | $CCl_4$ | Reflux | $CH_3$ Chlorination Mostly Ring | Monochloro-84% Dichloro-12% Mostly Ring |

Table I-continued

| Example | Initiator | Initiator as % by wt. of (IV) | Solvent | Reaction Temp °C | Results by VPC | Results by NMR |
|---|---|---|---|---|---|---|
| 7 | AIBN | 0.1 | CCl$_4$ | Reflux | Chlorination Mostly CH$_3$ | Chlorination |
| 8 | AIBN | 10 | Benzene | Reflux | Chlorination Mostly Ring | Monochloro-51% Mostly Ring |
| 9 | AIBN | 10 | ClCH$_2$CH$_2$Cl | Reflux | Chlorination Mostly Ring | Chlorination Mostly Ring |
| 10 | AIBN | 10 | Chlorobenzene | 80-90 | Chlorination | Chlorination |
| 11 | 2-t-butylazo-2-cuyanopropane | 10 | CCl$_4$ | Reflux | CH$_3$ Chlorination | |
| 12 | 2-t-butylazo-2-cyanobutane | 10 | CCl$_4$ | Reflux | Significant Ring Chlorination | Significant Ring Chlorination IV - 20% |
| 13 | Benzoyl Peroxide | 10 | CCl$_4$ | Reflux | Mostly CH$_3$ Chlorination | Monochloro-53% Dichloro-27% |
| 14 | Lauroyl Peroxide | 10 | CCl$_4$ | Reflux | Mostly CH$_3$ Chlorination | Low Conversion |

EXAMPLES 15 to 20

Evaluation of chlorine gas as a chlorinating agent, for the side chain chlorination of m-phenoxytoluene under various reaction conditions

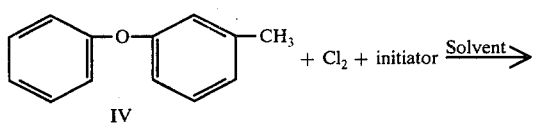

IV

General Procedure

A mixture of m-phenoxytoluene (IV; 5.0 g), an initiator (if any) and the solvent selected (20 ml) is heated to reflux and chlorine gas is bubbled through the refluxing mixture. After the addition of chlorine gas is completed, the reaction mixture is heated at reflux, up to 18 hours before sampling. After the desired reaction time is elapsed, samples are taken and evaporated in vacuo prior to estimating the percent composition by VPC and NMR. VPC analyses are obtained with a column 85 cm × 0.6 cm O.D. packed with 10% OV-17 on gas-chrom Q at 175° C. The retention times are as follows:

IV — 2.4 minutes
II — 8.0 minutes
III — 12.4 minutes
V — 5.6 minutes

The structure of (V) is consistent with the mass spectrum and C$^{13}$ nuclear magnetic resonance spectrum. Proton NMR chemical shifts for compounds II, III, IV and V are: II — 4.45 δ; III — 6.57 δ; IV — 2.25 δ; V — 2.2-2.3 δ.

Table II

| Example | Initiator | Initiator as % by wt. of (IV) | Solvent | Reaction Temp °C | Results by VPC | Results by NMR |
|---|---|---|---|---|---|---|
| 15 | None | — | CCl$_4$ | Reflux | Very little Reaction | |
| 16 | AIBN | 10 | CCl$_4$ | Reflux | CH$_3$ chlorination | Major Product:III some trichloromethyl Formed |
| 17 | Sunlamp | — | CCl$_4$ | Reflux | CH$_3$ chlorination Mostly Ring | Major Product:II Approx. 87% Ring |
| 18 | Sunlamp | — | CCl$_4$ | 0-40 | Chlorination Mostly Ring | Chlorination Mostly ring |
| 19 | Sunlamp | — | CH$_2$Cl$_2$ | Reflux | Chlorination Mostly CH$_3$ Chlorination | Chlorination |
| 20 | Sunlamp | — | Benzene | Reflux | Trace Ring Chlorination | Trace Ring Chlorination |

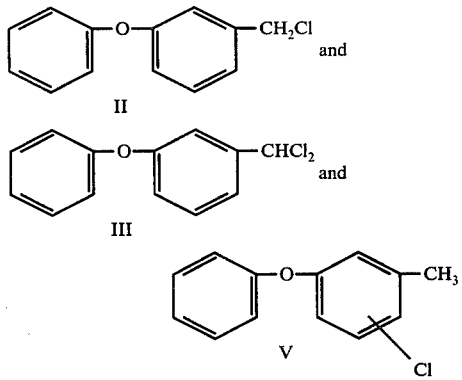

EXAMPLE 21

Evaluation of the light initiated chlorination of m-phenoxytoluene in refluxing carbon tetrachloride, using chlorine gas as the chlorinating agent

General Procedure

A solution of m-phenoxytoluene (38.5 g; 0.21 mole) in carbon tetrachloride (200 ml) is heated at reflux and irradiated with a G.E. 275 W. sunlamp. Chlorine gas is added to the refluxing solution. At various intervals, the reaction is interrupted to obtain a sample for analysis by vapor phase chromatography (VPC). The weight of chlorine delivered from a tared cylinder is recorded at this time, although there is some loss of chlorine from the reaction mixture. The data obtained by VPC analysis (6 ft. glass column ¼" I.D.; packed with 3% OV-17; temperature 200° C) are summarized in Table III.

When 34 g of chlorine has been added, the reaction mixture is cooled and evaporated in vacuo to yield 40.3 g of an orange oil. NMR analysis indicates the following, approximate, weight percent composition:

IV — 4.5%

II — 52.0%
III — 43.5%

The above NMR data account for 16.5 g of the 34 g of chlorine used in the course of the reaction.

Although the final ratio of II and III as determined by VPC and NMR are not in complete agreement, both analytical procedures confirm the low level of ring chlorination (less than 5%) as indicated by Examples 15 to 20.

Table III

| Interval | Wt. of Cl₂ Added in g | Equivalent Cl₂ | VPC - Approximate Area Product | | | |
|---|---|---|---|---|---|---|
| | | | IV | II | III | V |
| 1 | 15 | 1 | 81.7 | 14.8 | 0.5 | 3.0 |
| 2 | 19 | 1.27 | 44.6 | 48.3 | 3.1 | 4.0 |
| 3 | 20 | 1.34 | 40.3 | 51.5 | 4.3 | 3.8 |
| 4 | 25 | 1.68 | 27.0 | 59.1 | 10.9 | 3.0 |
| 5 | 30 | 2.01 | 7.3 | 74.0 | 21.8 | 4.2 |
| 6 | 31.5 | 2.11 | 6.0 | 67.7 | 27.5 | 3.7 |
| 7 | 34.0 | .28 | 4.1 | 66.5 | 26.0 | 3.4 |

EXAMPLE 22

Preparation of the α-cyanobenzyl esters by reaction of m-phenoxybenzaldehyde and the acid chlorides in the presence of an alkali cyanide A mixture of 0.05 gram-mole of m-phenoxybenzaldehyde and 0.05 gram-mole of 3,3-dimethylspiro[cyclopropane-1,1'-indene]-2-carboxylic acid chloride is added slowly, portionwise, to a solution of 0.075 gram-mole of potassium cyanide in 100 ml of water at 5° C. the mixture is stirred for 1.5 hours at 5° and then extracted with three 50—ml portions of ether. The extracts are washed with 10% hydrochloric acid solution, saturated sodium bicarbonate solution, and water and then dried over sodium sulfate. Removal of the ether under vacuum leaves α-cyano-m-phenoxybenzyl 3,3-dimethylspiro[cyclopropane-1,1'-indene]-2-carboxylate as a yellow-brown oil which is a useful insecticide as taught in U.S. Pat. No. 3,966,959 (1976).

We claim:

1. A process for the preparation of a compound of formula:

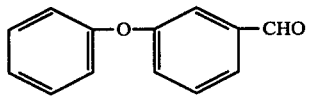

comprising halogenating with bromine, chlorine or sulfuryl chloride a compound of formula:

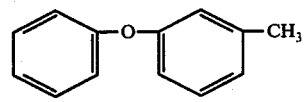

in a solvent of carbon tetrachloride or benzene with 1.2 to 2 molar equivalents of the halogenating agent at about the boiling point of the solvent selected, in the presence of 0.5% to 10% by weight of the formula (IV) compound of a free radical initiator of 2,2'-azobis(2-methylpropionitrile, 2-t-butylazo-2-cyanopropane, lauroyl peroxide or benzoyl peroxide for a period of time sufficient to essentially complete the reaction and obtain a mixture of compounds of formulae:

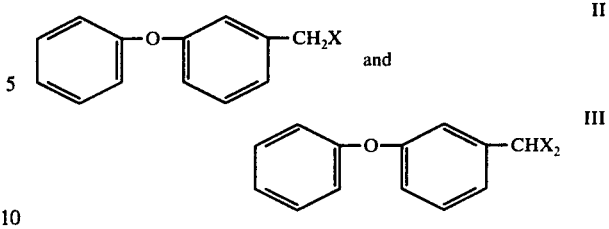

wherein X is a bromine or chlorine
reacting the halogenated mixture with 1.0 to 2.0 molar equivalents of hexamethylenetetramine in a solvent of aqueous $C_1$-$C_3$ alcohol or aqueous $C_2$-$C_3$ alkanoic acid; and
hydrolyzing the thus obtained mixture with a dilute mineral acid.

2. A process according to claim 1, wherein the solvent is carbon tetrachloride, the halogenating agent is bromine, the free radical initiator is 2,2'-azobis-(2-methylpropionitrile) present to the extent of 0.5% to 10% by weight of formula (IV) compound, X is bromine and the mineral acid is hydrochloric acid.

3. A process according to claim 1, wherein the halogenating agent is sulfuryl chloride, the free radical initiator is 2,2'-azobis-(2-methylpropionitrile) present to the extent of 0.5 to 10% by weight of formula (IV) compound, X is chlorine and the mineral acid is hydrochloric acid.

4. A process according to claim 1, wherein the the halogenating agent is sulfuryl chloride, the free radical initiator is 2-t-butylazo-2-cyanopropane or benzoyl peroxide present to the extent of 0.5% to 10% by weight of formula (IV) compound, X is chlorine, and the mineral acid is hydrochloric acid.

5. A process according to claim 1, wherein the halogenating agent is chlorine, the free radical initiator is 2,2'-azobis-(2-methylpropionitrile) present to the extent of 0.5% to 10% by weight of formula (IV) compound, X is chlorine and the mineral acid is hydrochloric acid.

6. A process according to claim 1, wherein the halogenating agent is chlorine, the free radical initiator is 2-t-butylazo-2-cyanopropane or benzoyl peroxide present to the extent of 0.5% to 10% by weight of formula (IV) compound, X is chlorine and the mineral acid is hydrochloric acid.

7. A process according to claim 1, wherein the mixture of m-phenoxybenzyl chloride (II) and m-phenoxybenzal chloride (III) (X = chlorine) is reacted with 1 to 2 molar equivalent of hexamethylenetetramine in hot aqueous ethanol or hot aqueous acetic acid and hydrolyzing the mixture with dilute hydrochloric acid to yield m-phenoxybenzaldehyde (I).

8. A process according to claim 1, wherein the mixture of m-phenoxybenzyl bromide (II) and m-phenoxybenzal bromide (X = bromine) is reacted with 1 to 2 molar equivalents of hexamethylenetetramine in hot aqueous ethanol or hot aqueous acetic acid and hydrolyzing the mixture with dilute hydrochloric acid to yield m-phenoxybenzaldehyde (I).

9. A process for the preparation of a compound of formula:

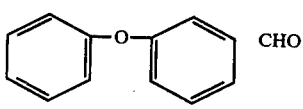 CHO    I comprising halogenating with bromine, chloride or sulfuryl chloride a compound of formula:

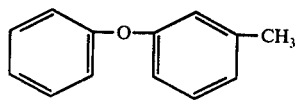

in a solvent of carbon tetrachloride or benzene with 1.2 to 2 molar equivalents of the halogenating agent at about the boiling point of the solvent selected, in the presence of a strong incandescent light source to activate the halogenating reaction for a period of time sufficient to essentially complete the reaction and obtain a mixture of compound of formulae:

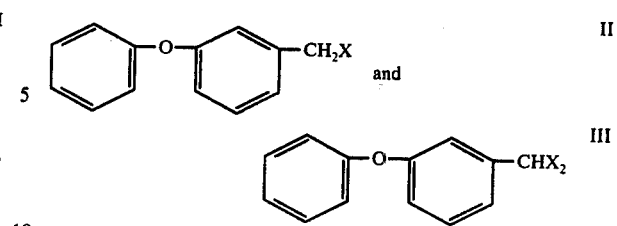

wherein X is bromine or chlorine
reacting the halogenated mixture with 1.0 to 2.0 molar equivalents of hexamethylenetetramine in a solvent of aqueous $C_1$–$C_3$ alcohol or aqueous $C_2$–$C_3$ alkanoic acid; and
hydrolyzing the thus obtained mixture with a dilute mineral acid.

10. A process according to claim 9, wherein the halogenating agent is chlorine, the reaction mixture is irradiated with an incandescent light source, X is chlorine and the mineral acid is hydrochloric acid.

* * * * *